US00PP28212P3

(12) United States Plant Patent
Bunnik

(10) Patent No.: US PP28,212 P3
(45) Date of Patent: Jul. 18, 2017

(54) ***GUZMANIA* PLANT NAMED 'G9197'**

(50) Latin Name: ***Guzmania Ruiz* et. Pav.**
Varietal Denomination: G9197

(71) Applicant: 3B Fundus BV, Kudelstaart (NL)

(72) Inventor: Bjorn Bunnik, De Kwakel (NL)

(73) Assignee: 3B Fundus BV, Kudelstaart (NL)

( * ) Notice: Subject to any disclaimer, the term of this patent is extended or adjusted under 35 U.S.C. 154(b) by 97 days.

(21) Appl. No.: 14/757,183

(22) Filed: Dec. 1, 2015

(65) Prior Publication Data

US 2016/0157406 P1 Jun. 2, 2016

(30) Foreign Application Priority Data

Dec. 1, 2014 (QZ) ..... PBR 2014/3208

(51) Int. Cl.
*A01H 5/12* (2006.01)

(52) U.S. Cl.
USPC ..... Plt./371

(58) Field of Classification Search
USPC ..... Plt./263.1, 370, 371
See application file for complete search history.

*Primary Examiner* — Susan McCormick Ewoldt
*Assistant Examiner* — Karen Redden
(74) *Attorney, Agent, or Firm* — Samuel R. McCoy, Jr.

(57) ABSTRACT

A new and distinct *Guzmania* cultivar named 'G9197' which is characterized by the combination of strongly reflexed foliage, leaf margins that undulate near the distal end and apex, compact and wide inflorescence, large floral bracts, floral bracts with a light purple general tonality, and the stability of all characteristics from generation to generation.

3 Drawing Sheets

Latin name of the genus and species: The Latin name of the genus and species of the novel variety disclosed herein is *Guzmania* Ruiz et. Pav.

Variety denomination: The inventive variety of *Guzmania* disclosed herein has been given the variety denomination 'G9197'.

CROSS REFERENCE TO RELATED APPLICATIONS

This application claims priority to the Community Plant Variety Rights application number 2014/3208, filed Dec. 1, 2014, which is herein incorporated by reference.

BACKGROUND OF THE INVENTION

Parentage: The *Guzmania* variety 'G9197' originated as a naturally occurring, whole-plant mutation of *Guzmania* 'Voila' (not patented). The inventor of 'G9197' is a commercial ornamental plant producer whom has produced 'Voila' for many years. As early as 2006, the inventor was actively monitoring for, and selecting mutations of, 'Voila' at his greenhouse operation in Kudelstaart, The Netherlands. Said mutations were selected on criteria such as compactness of the plant, inflorescence color, size of the inflorescence, compactness of the inflorescence, and foliage color. The variety now called 'G9197' was initially discovered in August of 2009 as one such mutation of the parent plant. For a small number of those mutations which exhibited commercial potential, including 'G9197', mericloning was initiated at a commercial laboratory in Roelofarendsveen, Netherlands. The resulting plantlets of each candidate variety were subsequently grown to a mature size. From these mature plants, a small number of basal offshoots were harvested from each variety, replanted, and again grown to a mature size for further evaluation. After further observation, the variety now called 'G9197' was finally selected in 2012 for its unique foliage and inflorescence characteristics.

Asexual Reproduction: 'G9197' was first asexually propagated by meristematic tissue culture in 2010 at a commercial laboratory in Roelofarendsveen, Netherlands. 'G9197' has since been asexually reproduced through seven additional generation by way of vegetative propagation using basal offshoots harvested from germplasm stock plants. Through these subsequent generations, the unique features of this cultivar have been stable and reproduced true to type.

SUMMARY OF THE INVENTION

The cultivar 'G9197' has not been observed under all possible environmental conditions and the phenotype may vary somewhat with variations in environment such as temperature, day length, and light intensity, without, however, any variance in genotype. The following traits have been repeatedly observed and are determined to be the unique characteristics of 'G9197'. These characteristics, in combination, distinguish 'G9197' as a new and distinct *Guzmania* cultivar:

1. 'G9197' exhibits strongly reflexed foliage; and
2. 'G9197' exhibits foliage with undulating margins near the distal end and apex; and
3. 'G9197' exhibits a compact and wide inflorescence; and
4. 'G9197' exhibits inflorescence with large floral bracts; and
5. 'G9197' exhibits floral bracts with a light purple general tonality.

BOTANICAL DESCRIPTION OF THE PLANT

Figure 1:
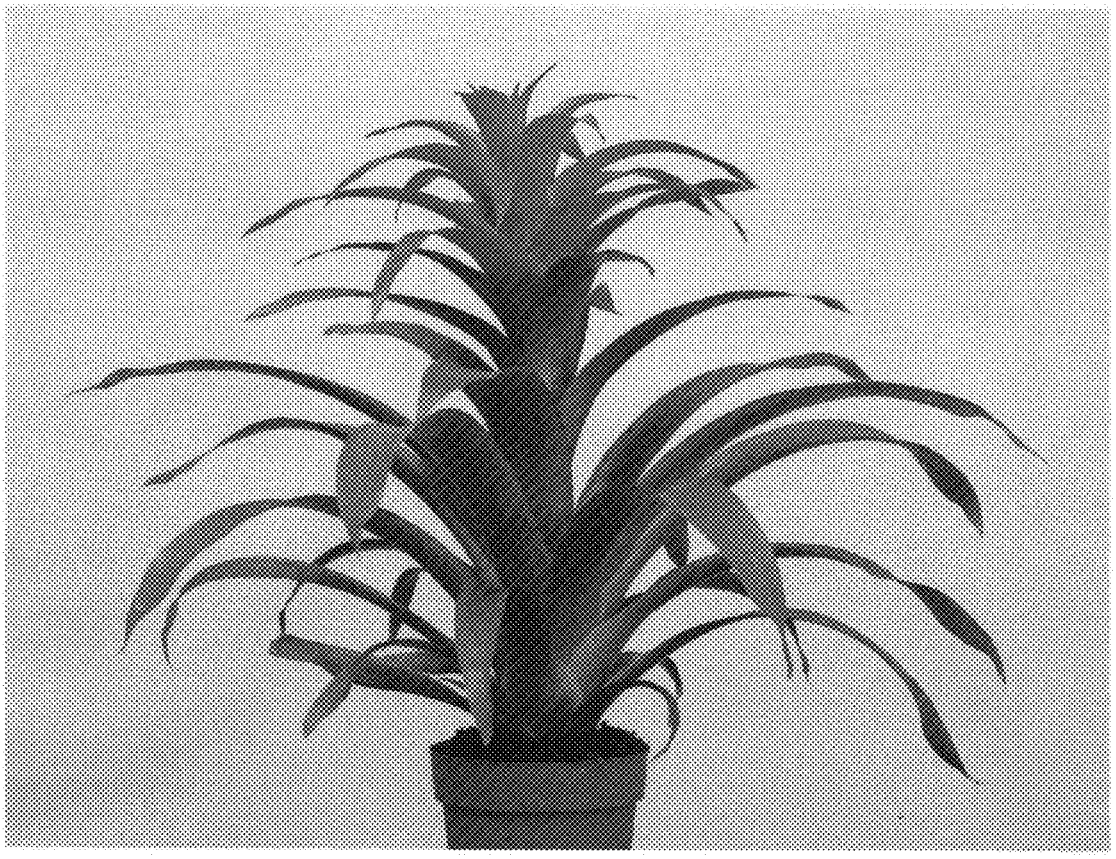
FIG. 1 illustrates, as nearly true as it is reasonably possible to make the same in color photographs of this type, an exemplary plant of 'G9197' grown in a commercial greenhouse in De Kwakel, The Netherlands. This plant is approximately 42 weeks old, shown planted in a 12 cm container.
Figure 2:
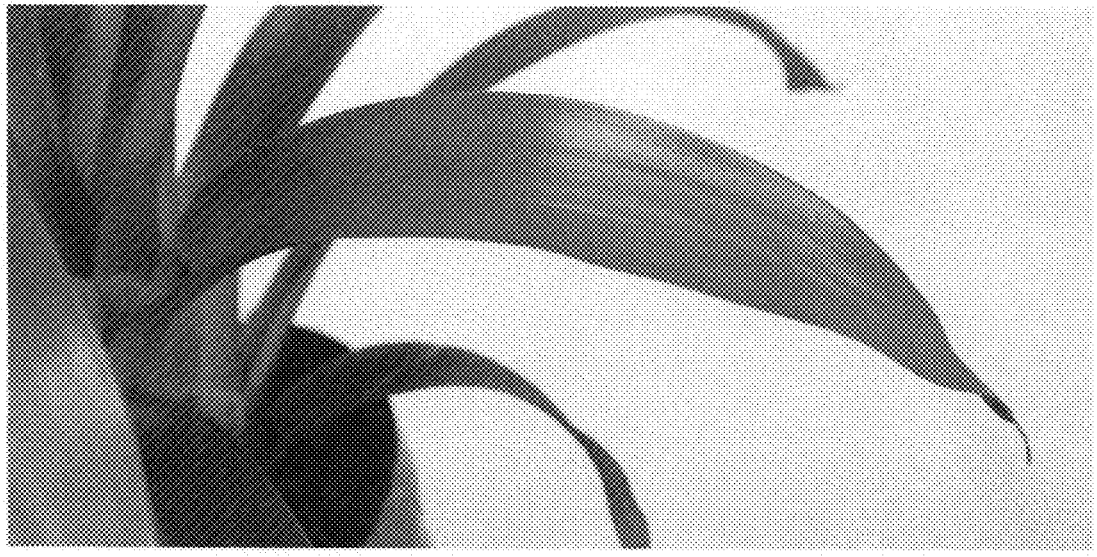
FIG. 2 illustrates, as nearly true as it is reasonably possible to make the same in color photographs of this type, the typical foliage of 'G9197'.
Figure 3:
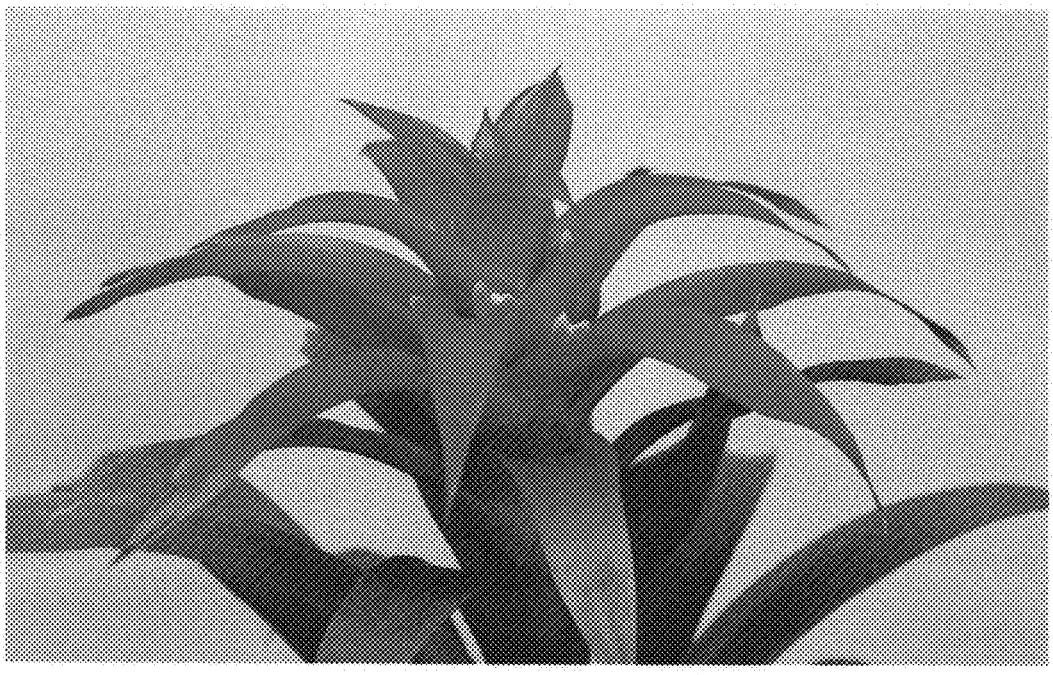
FIG. 3 illustrates, as nearly true as it is reasonably possible to make the same in color photographs of this type, the typical inflorescence of 'G9197'.

The following observations and measurements made in November of 2015 describe averages from a sample set of six specimens of 42 week-old 'G9197' plants grown in 12 cm nursery pots at a commercial greenhouse in De Kwakel, The Netherlands. During the growing season, plants were grown under shade cloth with daily light levels of approximately 100 to 150 mmol. In winter, supplemental light was used to maintain appropriate light levels. Plants were maintained with a weekly fertigation program and regularly watered with overhead irrigation. No chemical pest measures were taken.

Those skilled in the art will appreciate that certain characteristics will vary with older or, conversely, with younger plants. 'G9197' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climactic and cultural conditions. Color notations are based on *The Royal Horticultural Society Colour Chart*, The Royal Horticultural Society, London, 2015 (sixth edition).

A botanical description of '09197' and comparisons with other varieties of *Guzmania* are provided below.

Plant description:

- *Growth habit*.—Perennial; monopodial, upright. Leaves arranged in a basal rosette and the inflorescence grows from the center of the basal rosette.
- *Average height*.—24.7 cm, from the soil level to the top of the foliar plane, and 36.0 to the top of the floral plane.
- *Plant spread*.—Average of 51.3 cm.
- *Growth rate*.—Moderate.
- *Propagation type*.—Vegetative cuttings and mericloning.
- *Time to initiate roots*.—Approximately 14 to 28 days to initiate roots at 22 degrees Celsius.
- *Time to produce a rooted cutting*.—Approximately 105 days to initiate roots at 22 degrees Celsius.
- *Disease resistance or tolerance*.—Similar to other *Guzmania* varieties.
- *Pest resistance or tolerance*.—Similar to other *Guzmania* varieties.
- *Temperature tolerances*.—USDA Zones 10 to 12; at least tolerant of temperatures to 40 degrees Celsius. High tolerance to rain inundation; high tolerance to wind.

Root system:

- *General*.—Thick; medium density.
- *Texture*.—Slightly fleshy.

Foliage:

- *Arrangement*.—Basal rosette. No stems or lateral branches, the leaves form a stem-like structure not consisting of a stem as such, but only consisting of the leaf sheaths.
- *Lamina*.—Dimensions — 30.3 cm long and 4.2 cm wide. Thickness — Approximately 0.9 cm. Shape of blade — Ligulate; slightly concave. Aspect — Leaves held at an angle of approximately 60 degrees from horizontal and strongly reflexed (approximately minus −50 degrees from horizontal). Apex — Acuminate. Base — Sheathing. Margin — Entire and slightly undulated towards the apex. Pubescence, texture and luster of adaxial surface — Glabrous, smooth and moderately glossy. Pubescence, texture and luster of abaxial surface — Glabrous, smooth and moderately glossy. Color — Juvenile foliage, adaxial surface — Green, RHS 143A. Juvenile foliage, abaxial surface — Green to yellow-green, in between RHS 143A and 146A. Mature foliage, adaxial surface — Green to yellow-green, in between RHS 143A and 146A yet darker; proximal half of upper leaves are tinged red-purple, RHS 60C. Mature foliage, abaxial surface — Green to yellow-green, in between RHS 143A and 146A; proximal half of upper leaves are tinged red-purple, RHS 60C. Venation — Parallel. Mature foliage venation, adaxial surface — Green to yellow-green, in between RHS 143A and 146A yet darker. Mature foliage venation, abaxial surface — Green to yellow-green, in between RHS 143A and 146A.
- *Sheath*.—Sheath length — Average 11.0 cm. Sheath width — Average 7.1 cm. Sheath color — Adaxial surface is greyed-yellow, RHS 161A. Abaxial surface is greyed-yellow, RHS 162A, with a greyed-orange center, near N167A to N167B.

Inflorescence:

- *Inflorescence arrangement*.—Terminal compound spike with showy bracts and consisting of an average of 15 clusters of 9 individual flowers each.
- *Natural flowering season*.—Autumn into winter.
- *Time to flower*.—Approximately 9 months.
- *Inflorescence quantity*.—One.
- *Flowers per inflorescence*.—Average of 135, all in bud stage and not opening.
- *Inflorescence height*.—Approximately 12.0 cm (measured from base of lowest flower to top of upper flower).
- *Inflorescence diameter*.—Average of 5.1 cm, excluding bracts, and 25.9 cm with bracts.
- *Peduncle*.—Dimensions — Approximately 23.0 cm long, to the base of the inflorescence, and 1.0 cm wide. Aspect — Approximately 90-degree angle to horizontal. Strength — Strong. Texture and luster — Glabrous and slightly glossy. Color — Yellow-green, RHS 150D.

Bud:

- *Length*.—Average of 2.5 cm.
- *Diameter*.—Average of 0.4 cm; 0.15 cm at the narrowest point; bud is flattened.
- *Shape*.—Lanceolate.
- *Texture and luster*.—Glabrous and slightly glossy.
- *Color*.—White, RHS 155D.

Flower:

*Flower type and form.*—Single; not opening from bud-stage.

*Aspect.*—Upright.

*Height.*—Approximately 2.5 cm.

*Diameter.*—Average of 0.4 cm.

*Depth.*—Approximately 0.15 cm.

*Fragrance.*—No fragrance.

*Lastingness.*—30 days.

*Persistent.*—Persistent.

*Petals.*—Quantity of Petals — 3. Arrangement — Rotate; single whorl of unfused petals. Length — Approximately 0.7 cm. Width — Approximately 0.2 cm. Shape — Ovate to oblong. Apex — Obtuse. Base — Cuneate. Margin — Entire. Pubescence, texture and luster of upper surface — Glabrous, smooth and slightly glossy. Pubescence, texture and luster of lower surface — Glabrous, smooth and moderately glossy. Color when opening, upper surface — Greyed-orange, RHS 165B. Color when opening, lower surface — Greyed-orange, RHS 165B. Color when fully opened, upper surface — Greyed-orange, RHS 165B. Color when fully opened, lower surface — Greyed-orange, RHS 165B. Fading, upper surface — Not fading. Fading, lower surface — Not fading. Venation color, fully opened, upper surface — Greyed-orange, RHS 165B. Venation color, fully opened, lower surface — Greyed-orange, RHS 165B.

*Calyx.*—Shape — Rotate. Length — Average of 2.5 cm. Diameter — Calyx is flattened; average diameter at widest point is 0.4 cm and diameter at narrowest point is an average of 0.15 cm.

*Sepals.*—Quantity — 3 unfused sepals. Arrangement — Rotate. Length — 2.0 cm. Width — 0.4 cm. Shape — Lanceolate when unfolded. Apex — Broad acute. Base — Cuneate. Margin — Entire. Pubescence, texture and luster of upper surface — Glabrous, velvety, and moderately glossy. Pubescence, texture and luster of lower surface — Glabrous, velvety, and moderately glossy. Color when opening, upper surface — White, RHS NN155A. Color when opening, lower surface — White, RHS NN155A. Color when fully opened, upper surface — White, RHS NN155A. Color when fully opened, lower surface — White, RHS NN155A.

*Bract.*—General — One large, colorful bract is placed below each cluster of individual flowers and each individual flower is also enclosed by a bract. Large bracts below each cluster — Quantity — Average of 15. Shape — Ligulate. Dimensions — Average of 11.4 cm long and 3.0 cm wide. Apex — Acuminate; slightly twisted at the extreme distal end. Base — Sheathing. Margins — Entire. Upper bract color, upper surface — Red-purple, RHS 60B, and darker towards the apex, RHS 59B. Upper bract color, lower surface — Red-purple, RHS 60C. Lower bract color, upper surface — Red-purple, RHS 60B, with apex yellow-green, RHS 147A. Lower bract color, lower surface — Red-purple, RHS 60B, with apex yellow-green, RHS 148A. Sheath — Sheath length — Average 4.0 cm. Sheath width — Average 5.9 cm. Sheath color, upper surface — Greyed-yellow; 160A to 160B. Sheath color, lower surface — Greyed-yellow to grey-brown; in between 161A and N199D. Bracts that enclose each flower — Quantity — Average of 9. Shape — Oblong; folded. Dimensions — Average of 4.2 cm long and 2.0 cm wide, at the widest point. Apex — Acute. Base — Broad cuneate. Margins — Entire. Color, upper and lower surfaces — White, RHS 155A to 155B; apex is red-purple, RHS 67A; apex of inner bracts lack the red-purple coloration.

Reproductive organs:

*Stamens.*—Quantity — Three, on average. Anthers — Shape — Basifixed; narrow oblong. Dimensions — Average of 0.4 cm long and 0.1 cm wide. Color — Greyed-yellow, RHS 161D. Filaments — Length — 0.05 cm, on average. Color — Greyed-yellow, RHS 161D. Pollen — None detected.

*Pistil.*—Quantity — One, on average. Length — 0.5 cm. Style — Length — 0.4 cm. Color — Brown, RHS 200A. Stigma — Shape — Club-shaped. Dimensions — Average of 0.1 cm long and 0.05 cm wide. Color — Brown, RHS 200C. Ovary Color — White, RHS 155A.

Fruit and seed: To date, not observed.

COMPARISONS WITH THE PARENT PLANT

'G9197' is similar in many horticultural characteristics to its parent plant, *Guzmania* 'Voila'. However 'G9197' differs from its parent in the following characteristics:

1. The leaves of 'G9197' are held at an angle of approximately 60 degrees from horizontal and reflexed to approximately minus −50 degrees from horizontal, whereas the leaves of Voila' are held at an angle of approximately 65 degrees from horizontal and reflexed to approximately minus −40 degrees from horizontal.
2. The leaves of 'G9197' are an average of 4.2 cm wide, whereas the leaves of 'Voila' are an average of 3.5 cm.
3. The leaf margins of 'G9197' are undulating near the distal end, whereas the leaf margins of 'Voila' lack this undulation.
4. The average length of the large bracts of 'G9197' is 11.4 cm, whereas the average length of the large bracts of 'Voila' is 8.6 cm.
5. The average width of the large bracts of 'G9197' is 3.0 cm, whereas the average width of the large bracts of 'Voila' is 2.6 cm.
6. The larger bracts of 'G9197' exhibit a slightly lighter purple general tonality when compared to the large bracts of 'Voila'.
7. The upper large bracts of 'G9197' are a solid color, whereas the upper large bracts of 'Voila' are tinged with yellow-green.

COMPARISON WITH THE MOST SIMILAR *GUZMANIA* CULTIVAR KNOWN TO THE INVENTOR

'G9197' is similar in many horticultural characteristics to the commercial cultivar *Guzmania* 'Alerta' (Community Plant Variety Rights grant number 12732). However 'G9197' differs from 'Alberta' in the following characteristics:

1. The total inflorescence height of 'G9197' ranges from 35 to 50 cm, whereas the total inflorescence height of 'Alberta' ranges from 50 to 65 cm.

2. The inflorescence diameter of 'G9197' ranges from 20 to 25 cm, whereas the inflorescence diameter of 'Alberta' ranges from 12 to 20 cm.
3. The general appearance of the 'G9197' inflorescence is compact and wide, whereas the general appearance of the 'Alberta' is tall and narrow.
4. The foliage aspect of 'G9197' is strongly reflexed, whereas the foliage of 'Alberta' lacks reflexing.
5. The foliage of 'G9197' exhibits a lighter green general tonality when compared to the general tonality of the 'Alberta' foliage.

That which is claimed is:

1. A new and distinct variety of *Guzmania* plant named 'G9197', substantially as described and illustrated herein.

* * * * *